United States Patent

Bodenschatz

[11] Patent Number: 6,129,694
[45] Date of Patent: Oct. 10, 2000

[54] METHOD FOR FASTENING PADS TO MEDICAL BANDAGES

[75] Inventor: Stefan Bodenschatz, Buxtehude, Germany

[73] Assignee: Beiersdorf, Hamburg, Germany

[21] Appl. No.: 08/601,914

[22] Filed: Feb. 15, 1996

[30] Foreign Application Priority Data

Feb. 22, 1995 [DE] Germany ............... 195 06 128

[51] Int. Cl.[7] .............................................. A61F 13/00
[52] U.S. Cl. ........................ 602/60; 602/61; 602/62
[58] Field of Search .................. 602/41–59, 60, 602/61, 62, 63, 20, 23, 21, 26, 27; 128/888, 889, 893, 894; 2/455

[56] References Cited

U.S. PATENT DOCUMENTS

| | | | |
|---|---|---|---|
| 4,166,464 | 9/1979 | Korpman | 602/58 |
| 4,655,210 | 4/1987 | Edenbaum et al. | 602/46 |
| 5,027,801 | 7/1991 | Grim | 602/18 X |
| 5,445,604 | 8/1995 | Lang | 602/47 |
| 5,496,358 | 3/1996 | Rosenwald | 607/108 |
| 5,792,084 | 8/1998 | Wilson et al. | 602/13 |

*Primary Examiner*—Kim M. Lee
*Attorney, Agent, or Firm*—Norris, McLaughlin & Marcus, P.A.

[57] ABSTRACT

A method for fastening pads to medical bandages, stockings and the like, wherein the pad is welded by thermal action or by cementing between two support materials of film, fabric, knit material or fleece, of which at least one consists of a thermoplastic material, is shaped substantially to its contour, and is fastened to the bandage by thermal action by means of the thermoplastic material which faces the side of the bandage. Preferably, the pad welded between the two support materials is punched out, cut out or the like according to its contour with an overhanging margin and fastened by means of the latter to the bandage.

12 Claims, 2 Drawing Sheets

METHOD FOR FASTENING PADS TO MEDICAL BANDAGES

BACKGROUND OF THE INVENTION

The invention relates to a method for fastening pads of cushions to medical bandages, e.g., for orthopedic purposes, compression stockings, burn dressings, and the like. Such products consist usually of elastic materials, chiefly woven or knit, and the pads or cushions can be in the form of pressure pads, pads which produce a massaging effect upon movement, or protective and supportive pads. they consist usually of elastic materials, such as silicone rubber or foam rubber, or of cushioning materials such as nonwovens, and they can have a great variety of forms.

DESCRIPTION OF PRIOR ART

The terms pads or cushions, as used herein, refer to any kind of shaped articles which are to act upon joints, muscles or tendons. Usually they consist of silicone rubber, synthetic rubber, rubber, foam, or other more or less elastic materials, e.g., including fleece. Also included are pressure pads with an integrated small, so-called friction core of hard or incompressible material according to European Patent 496,071 and U.S. Pat. No. 5,306,229, or only any such kind of more or less hard core, which can have a great variety of configurations and which, upon movement, exercises and especially effective and locally directed massage. For the sake of simplicity, only the term "pads" will be used, as a rule, hereinbelow, but all of these possible embodiments are meant.

Such pads are commonly fastened to the inside or outside of bandages by providing them with a covering that has approximately the shape of the pad and is stitched to the bandage along its circumferential margin. According to DE-C 3832 438 it is also known to fasten the covering by providing it on the side facing the pad with an elastic, thermoplastic synthetic resin coating and bonding it to the textile material of the bandages by heating along the margins. The welding or cementing of various textile materials with thermoplastic coatings or interlayers including thermoplastically elastic interlayers, is one procedure that has long been known in textile technology, as for example in DE-OS 14 60 008 and DE-OS 23 42 149 and others.

In the known methods for fastening the pads, the pads and the loose covering must be precisely positioned and fastened. This is all more difficult the more irregular the contours of the pad are—as is often the case with anatomically adapted pads—and the smaller the pad or cushion is the more difficult the more inaccessible its position is on the product.

It is an object of the present invention to arrange the fastening of such pads or cushions so that this will be easily possible and also easily possible even at hard-to-reach points on the bandage.

THE INVENTION

This and other objects are realized in accordance with the present invention pursuant to which there is provided a novel method for fastening a pad to a medical support such as a bandage, stocking, or the like, which comprises welding the pad by the action of heat or cementing the pad between two support materials of film, fabric, knit goods or fleece, at least one of which comprises a thermoplastic material, shaped substantially to its contour, and fastened to the support by means of a thermoplastic material which faces the side of the support.

Advantageously the pad welded between the two support materials is punched out or cut out to its contour with an overhanging margin. The pad may be fastened to the support by means of the overhanging margin at the outer contour, possibly only at individual points of the marginal area, the marginal area being enlarged at the points at which the pad is fastened.

More specifically, the pad is packed in a first step into a pocket matching its shape.

At least on the side of the pad which later will face the product, a thermoplastic, preferably thermoplastic-elastic support material in the form of film, tissue, knits or nonwovens, is used. Such materials are known, and consist for example of polyurethane, polyvinyl chloride or polyethylene.

On the other side an elastic, skin-friendly material is placed, such as a film, a mesh or a fabric—especially if the pad is applied to the inside of the bandage and thus comes to lie against the skin. The pad may be in the form of a hard, small body.

In accordance with the shape of the pad, the two materials are bonded together by local heating to soften the thermoplastic material. The heating can be performed, for example, by the hot sealing method with heated dies, or preferably by the high-frequency method.

In the same or in a subsequent step the encased pad is stripped out, i.e., preferably stamped out or severed by some other separating method, taking care not to damage the weld or seam. Preferably a margin of about 2–20 mm, advantageously 4–7 mm, is left remaining. In the case of the above-described friction cores or small shaped articles for a specific massage, the size of the pocket can also amount to only about 1 cm, and the remanent margin to only about 1 mm.

In an additional step, the pads enveloped in the manner described are fastened to the bandage by means of the thermoplastic side, preferably only over the margin extending beyond the outer contour. This is again performed by the application of heat, producing a bond over the entire area in which the pad is in contact with the bandage, or only over the projecting margin. Also, only partial fastening may be desirable in the area or particularly in the marginal area according the anatomical shape of the bandage, e.g., for the shoulder area. In this manner a certain freedom of movement of the pad can be achieved, while the marginal area that serves for fastening can be slightly enlarged so as to permit an especially stable fastening.

In the case of the small, shaped articles for a particular massaging action, a bond is preferably formed in the entire area in which the pad is in contact with the bandage, due to the small size of the pocket.

The support material enveloping the pad and afterward facing the bandage can be provided with one or more cutouts of any desired shape, e.g., round or oval, or also with interruptions such as slits, for example. Thus, in the case of bandages which are stretched in use, the effect of this thermoplastic and preferably elastic support material on the properties of the product after the pad is fastened can be controlled, e.g., by greater ability to stretch and yield. The opening or openings, however, must be made only so large that the pad will still held securely in the pocket before and during attachment to the bandage.

If dense materials, such as films or coated fabrics and knits, are used for wrapping the pad, then instead of a solid cushion a fluid, in the form of a gel or high-viscosity oil, can be packed and solidified by the method described. This results in cushions which permit a very uniform distribution of pressure. Another possibility is to fill the cavity with air.

The pads welded or sealed or cemented in place according to the invention can be further processed directly, i.e., they can be fastened to the bandages of the like, but they can also be stocked and then employed as needed. This is economically advantageous especially if the final manufacture of the bandages takes place separately from the manufacture and treatment of the pads.

In the case of bandages and pads of particularly simple kinds, the operations described can also be performed simultaneously. That is, the thermoplastic layer is placed on the bandage, and on it is placed the pad; on the pad the already largely completely shaped cover material is laid, and then the cover material is fastened on the bandage by means of the thermoplastic layer along the projecting margin.

The invention will be further described with reference to the accompanying illustrative drawing, wherein.

DETAILED DESCRIPTION OF THE INVENTION

Figure 1:
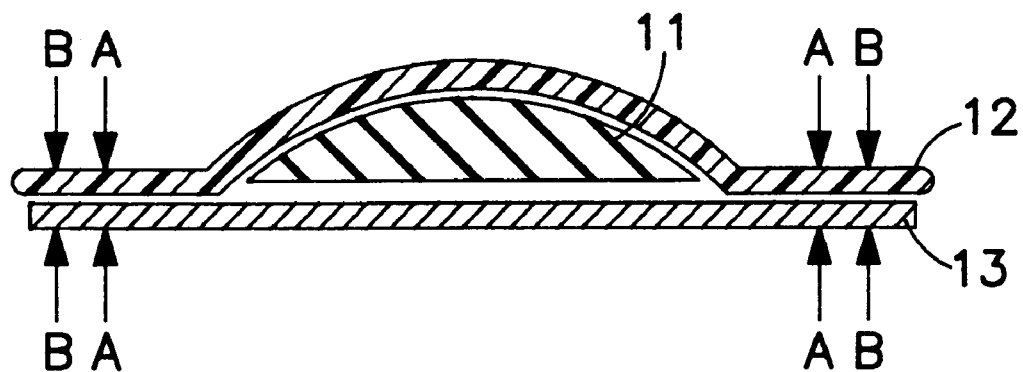
FIG. 1 is a vertical section through an assembly of pad and supports prior to welding in accordance with the invnetion.
Figure 2:
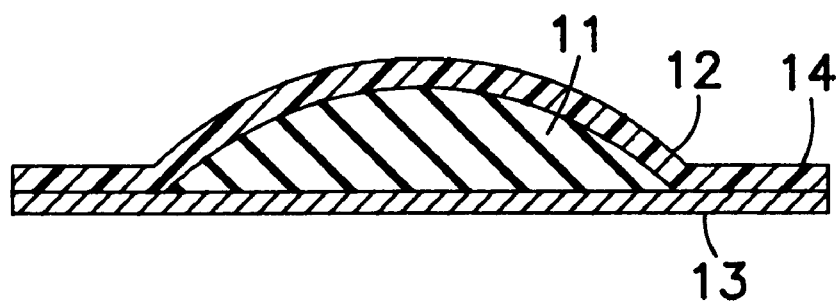
FIG. 2 is a vertical section through the assembly of FIG. 1 after welding.

Referring now more particularly to the drawing, in FIG. 1 there is shown the bonding of a pad by welding. (11) indicating a pad, (12) a cover material, (13) a thermoplastic support material, (A) a weld seam to which high-frequency electrodes are applied, (B) the location of a cut. FIG. 2 shows the pad welded in place with a projecting margin (14).

Figure 3:
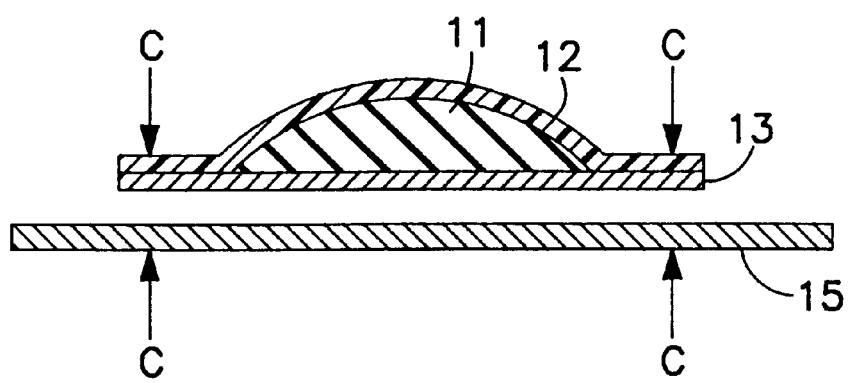
FIG. 3 shows how the assembly of FIG. 2 can be fastened to a bandage.

FIG. 3 shows how the fastening is performed on the bandage. A bandage material is indicated at (15), and a seam at which the pad is fastened to the bandage at (C).

Figure 4:
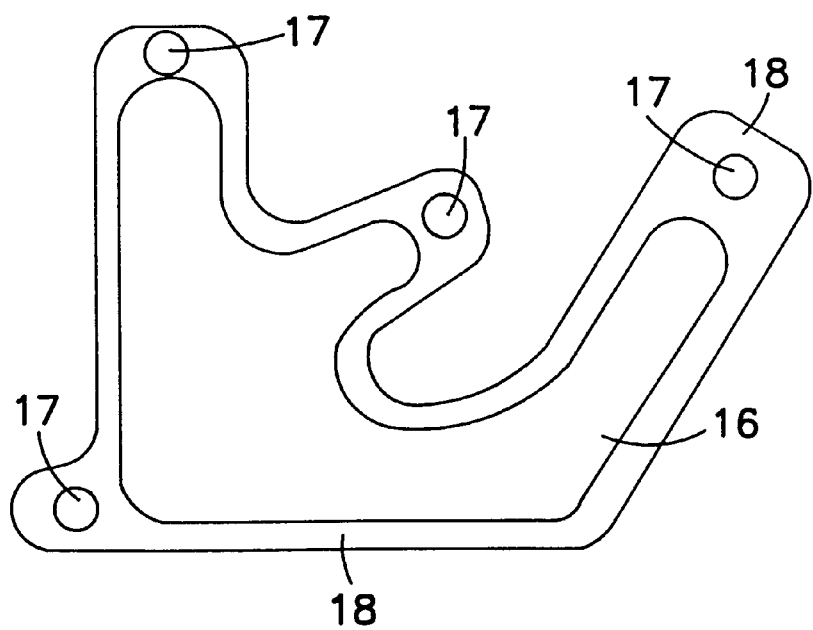
FIG. 4 is a plan view of an assembly including a pad of complex shape showing where it can be fastened to a bandage.

FIG. 4 shows a pad (16) of complex shape, which is fastened at individual points (17) to a bandage, not shown, by its projecting and partially widened margin (18).

The process according to the invention makes it possible to fasten pads and cushions to bandages of any shape, in a technically simple and economical manner, while even complicated shapes present no very great problems.

It will be understood that the specification and examples are illustrative but not limitative of the present invention and that other embodiments within the spirit and scope of the invention will suggest themselves to those skilled in the art.

What is claimed is:

1. A method for fastening a pad to a medical support comprising:

a) welding the pad by the action of heat or cementing the pad between two support materials selected from the group consisting of film, fabric, knit goods or fleece; and b) fastening the product of a) to the medical support by means of a thermoplastic material which faces a side of the medical support;

wherein at least one of the two support materials in a) comprises a thermoplastic material, shaped to the contour of the pad.

2. A method according to claim 1, wherein the pad welded between the two support materials is punched out or cut out to its contour with an overhanging margin.

3. A method according to claim 2, wherein the pad is fastened to the medical support by means of the overhanging margin at the outer contour.

4. A method according to claim 3, wherein the pad is fastened to the medical support only at individual points of the marginal area.

5. A method according to claim 4, wherein the marginal area is enlarged at the points at which the pad is fastened.

6. A method according to claim 1, wherein the thermoplastic film, the fabric, knit material or fleece comprises an elastic, thermoplastic material.

7. A method according to claim 1, wherein the thermoplastic support material which faces the bandage is provided with one or more cutouts or interruptions.

8. A method according to claim 1, wherein the pad is compressible.

9. A method according to claim 1, wherein the support materials between which the pad is welded or cemented are dense in comparison with the pad.

10. A medical bandage produced by the process of claim 1.

11. A method according to claim 1, wherein the medical support is selected from the group consisting of bandages and stockings.

12. A method according to claim 1, wherein steps a) and b) are carried out simultaneously.

* * * * *